United States Patent [19]

Fujii et al.

[11] Patent Number: 5,540,818
[45] Date of Patent: Jul. 30, 1996

[54] PROCESS FOR THE PRODUCTION OF HIGH PURITY METHANESULPHONYL FLUORIDE AT AN IMPROVED YIELD

[75] Inventors: Kenji Fujii; Tamio Nakamura, both of Ube; Yoshiyuki Kobayashi, Yokohama, all of Japan

[73] Assignee: Central Glass Co., Ltd., Yamaguchi-ken, Japan

[21] Appl. No.: 412,851

[22] Filed: Mar. 29, 1995

Related U.S. Application Data

[63] Continuation of Ser. No. 182,567, Jan. 18, 1994, abandoned.

[30] Foreign Application Priority Data

Jan. 18, 1993 [JP] Japan ............................... 5-005524

[51] Int. Cl.$^6$ ................................................ C07C 17/383
[52] U.S. Cl. .......................... 203/95; 203/39; 570/178
[58] Field of Search .................................. 203/95, 96, 92, 203/39; 570/178; 562/825

[56] References Cited

U.S. PATENT DOCUMENTS

| | | | |
|---|---|---|---|
| 3,920,738 | 11/1975 | Martin | 562/825 |
| 4,005,138 | 1/1977 | Plattner et al. | 562/825 |
| 4,285,778 | 8/1981 | Crosby | 203/95 |
| 4,683,090 | 7/1987 | Clark | 562/825 |
| 5,225,048 | 7/1993 | Yuan | 203/95 |

*Primary Examiner*—Robert Warden
*Assistant Examiner*—Robert Carpenter
*Attorney, Agent, or Firm*—Wenderoth, Lind & Ponack

[57] ABSTRACT

A process for producing methanesulfonyl fluoride involves reacting methanesulfonyl chloride, a metal fluoride and water to obtain a reaction product, subjecting the reaction product to distillation in the presence of water in an amount of 0.7 times or more the amount of the methanesulfonyl chloride to obtain a distillate. The distillate has a water layer and a methanesulfonyl fluoride layer. The distillate is subjected to phase separation to separate the methanesulfonyl fluoride layer from the water layer, and the methanesulfonyl fluoride is recovered.

5 Claims, No Drawings

PROCESS FOR THE PRODUCTION OF HIGH PURITY METHANESULPHONYL FLUORIDE AT AN IMPROVED YIELD

This application is a continuation of now abandoned application Ser. No. 08/182,567, filed Jan. 18, 1994.

BACKGROUND OF THE INVENTION

1. Field of the Invention

The present invention relates an improved process for producing methanesulfonyl fluoride useful as an intermediate in the production of medicaments or agricultural chemicals or as a starting material in the production of trifluoromethanesulphonic acid ($CF_3SO_3H$).

2. Related Background Art

Trifluoromethanesulphonic acid is generally produced by means of the electrochemical fluorination technique, wherein the use of methanesulphonyl fluoride as the starting material is more advantageous in comparison with the case of using methanesulphonyl chloride ($CH_3SO_2Cl$) as the starting material in that an improved yield can be attained with good current efficiency and without occurrence of chlorine gas.

Methanesulphonyl fluoride ($CH_3SO_2F$) is generally produced in the following manner. That is, a metal fluoride such as potassium fluoride (KF) is mixed with methanesulphonyl chloride ($CH_3SO_2Cl$), followed by reaction in the presence of a solvent such as water. (see, J. Chem. Soc. p. 178 (1956))

The reaction herein can be expressed by the following formula.

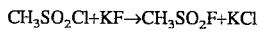

$$CH_3SO_2Cl + KF \rightarrow CH_3SO_2F + KCl$$

After the reaction has been completed, the resultant reaction product is subjected to distillation or filtration to separate methanesulphonyl fluoride ($CH_3SO_2F$) as the final product.

The above reaction is usually conducted while controlling the water content in the reaction system to a minimum with a due care about the reaction rate, because the methanesulphonyl chloride as the starting material has a property of being hydrolyzed, and the methanesulphonyl fluoride as the final product has a property of being hydrolyzed and also a property of being somewhat dissolved in water. In view of this, in the case of separating the methanesulphonyl fluoride from the reaction product obtained in the above reaction by means of the distillation manner, it is difficult to attain a desirably high yield.

As above described, it is possible to separate the methanesulphonyl fluoride from the reaction product obtained in the above reaction by means of the filtration method. However, disadvantages occur in this case such that the filtrate unavoidably contains by-products such as salts in addition to water and because of this, the successive purification process eventually become complicated.

SUMMARY OF THE INVENTION

The present invention is aimed at eliminating the problems in the foregoing conventional process of producing methanesulphonyl fluoride and providing an improved process to efficiently produce methanesulphonyl fluoride at an improved yield.

Another object of the present invention is to provide an improvement in the conventional process of producing methanesulphonyl fluoride based on the foregoing reaction formula and including the distillation separation manner to efficiently produce methanesulphonyl fluoride at an improved yield.

DESCRIPTION OF THE PREFERRED EMBODIMENTS OF THE INVENTION

The present inventors made extensive studies in order to eliminate the foregoing problems in the conventional process for the production of methanesulphonyl fluoride and in order to attain the above objects. Particularly, disregarding the common knowledge in the prior art that the water content in the reaction product of methanesulphonyl chloride and potassium fluoride be reduced as much as possible, the present inventors intentionally attempted to conduct the foregoing reaction between the methanesulphonyl chloride and metal fluoride in the presence of water at an increased content and subject the reaction product to distillation and as a result, obtained a finding that a marked improvement is attained in the yield of methanesulphonyl fluoride. The present invention has been accomplished based on this finding.

The present invention is directed to an improvement in a process of producing methanesulphonyl fluoride by reacting methanesulphonyl chloride with metal fluoride in the presence of water to obtain a reaction product contaning methanesulfonyl fluoride, subjecting the reaction product to distillation to obtain a distillate having lower and upper phases and separating the lower phase from the upper phase whereby methanesulphonyl fluoride is obtained, the improvement is characterized in that said distillation is conducted in the presence of water in an amount corresponding to 0.7 part by weight or above versus the amount of the methanesulphonyl chloride as a starting material.

In a preferred embodiment of the present invention, the amount of the metal fluoride dedicated for reaction with the starting methanesulphonyl chloride is made to be preferably in the range of 1 to 3 or more preferably in the range of 1 to 1.2 in terms of the equivalent ratio versus the amount of the methanesulphonyl chloride. In the case where the amount of the metal fluoride is made to be less than 1 in terms of the equivalent ratio versus the amount of the methanesulphonyl chloride, the reaction rate is markedly retarded to result in providing a remainder comprising non-reacted methanesulphonyl chloride. On the other hand, the use of the metal fluoride in an amount exceeding 3 in terms of the equivalent ratio versus the amount of the methanesulphonyl chloride does not provide any particular advantage and economically disadvantageous.

The metal fluoride usable in the present invention can include alkali metal fluorides such as NaF and KF, and acidic alkali metal fluorides such as KF.nHF and NaF.nHF. These metal fluorides may be used either singly or in combination of two or more of them. Among these metal fluorides, alkali metal fluorides are the most desirable, wherein the use of KF is particularly advantageous in the viewpoint of reaction rate, and the use of NaF is particularly advantageous in the economical viewpoint.

In the present invention, instead of the metal fluoride, it is possible to use other fluoride compounds such as $NH_4F$, $(NH_4)_2SiF_6$, $H_2SiF_6$, $Na_2SiF_6$, and HF.

The above-mentioned metal fluorides are different from each other in terms of the conditions upon their engagement in the reaction with the methanesulphonyl chloride. Especially, the desirable quantitative range for water to be added upon conducting the reaction with the methanesulphonyl chloride is different depending upon the kind of the metal fluoride used.

As above described, the reaction between the metal fluoride and methanesulphonyl chloride is conducted in the presence of water as the reaction medium, wherein the reaction proceeds under the condition that the metal chloride is dissolved in the water as the reaction medium. In the case where although the fluorine-supplying source (that is, a given metal fluoride) should be present in a sufficient amount against the methanesulphonyl chloride in the reaction system, the metal fluoride used is one having a small solubility against the water as the reaction medium and which is not sufficiently dissolved in the water, undissolved part of the metal fluoride is not dedicated for the reaction with the methanesulphonyl chloride wherein complete utilization of the metal fluoride is not attained. Thus, in this case, it is necessary to increase the amount of the water added to the reaction system in order to accomplish the reaction between the metal fluoride and methanesulphonyl chloride within a short period of time. Specifically, in the case of using NaF as the metal fluoride, the amount of the water to be added to the reaction system is desired to be in the range of 2.0 to 10.0 parts by weight versus the amount of the NaF. When the water content in the reaction system is less than 2.0 parts by weight versus the amount of the NaF, the reaction between the NaF and methanesulphonyl chloride cannot be accomplished within a short period of time, resulting in poor recovery of methanesulphonyl fluoride as the final product in the successive distillation step. When the water content in the reaction system exceeds 10.0 parts by weight versus the amount of the NaF, a desirable recovery is not attained for the final product methanesulphonyl fluoride resulted in the distillation step.

In the case of using KF as the metal fluoride, the amount of the water to be added to the reaction system is not necessary to be increased as in the case of using NaF, since it excels in solubility against water as the reaction medium. In this case, the reaction between the KF and methanesulphonyl chloride is accomplished within a short period of time in the presence of water in a relatively small amount in the reaction system.

In the present invention, it is desired for the reaction between the metal fluoride and methanesulphonyl chloride to be conducted at a temperature in the range of 20° to 60° C. When the reaction between the metal fluoride and methanesulphonyl chloride is conducted at a temperature exceeding 60° C., hydrolysis is liable to occur, resulting in decreasing the yield of the resulting methanesulphonyl fluoride.

In the present invention, the reaction product obtained as a result of the reactions between the metal fluoride and methanesulphonyl chloride is subjected to distillation to thereby separate methanesulphonyl fluoride, wherein methanesulphonyl fluoride is distilled together with water at a given vapor pressure. Thus, the amount of the water contained in the reaction product upon distilling the reaction product is the most important factor of governing the yield of the resulting methanesulphonyl fluoride. The control of the water content in the reaction product may be conducted after the reaction having been completed. In a preferred embodiment, it is conducted prior to the reaction in the viewpoint of considering the reaction rate. Specifically, in any case, the water added is controlled such that the water content in the reaction product is of an amount of 0.7 part by weight or above versus the amount of the methanesulphonyl chloride as the starting material.

In the case where the water content is of an amount of less than 0.7 part by weight versus the amount of the methanesulphonyl chloride as the starting material, by-products such as salts are liable to precipitate upon conducting the distillation of the reaction product, wherein desirable thermal efficiency is not provided and desirable distillation efficiency is not provided accordingly, and a result, desirable yield is not attained for the resulting final product methanesulphonyl fluoride. Further in the case of using the reaction vessel provided with a coil type heat exchanger, there is a tendency that a certain amount of the product having a high boiling point is remained without being distilled, resulting in making it difficult to attain a desirable yield for the resulting final product methanesulphonyl fluoride. Thus, it is also necessary to make a due care about the reaction apparatus used.

In the present invention, it is desired for the distillation of the reaction product to be conducted under reduced pressure condition in order to prevent occurrence of hydrolysis. Specifically, the distillation of the reaction product is conducted at a vacuum in the range of 50 to 100 Torr.

The process according to the present invention is desired to be conducted by using a relevant reaction apparatus provided with an appropriate mechanism capable of mixing raw materials so as to effectively cause chemical reaction among the raw materials and facilitating the chemical reaction. As a typical example of such reaction apparatus, there can be mentioned a reaction apparatus comprising a reaction vessel provided with a jacket temperature controlling mechanism and a stirring means, and a heat exchanger (this reaction apparatus will be hereinafter referred to as jacket type reaction apparatus).

In the process according to the present invention, the distillate caused as a result of the distillation of the reaction product has two phases one comprising an upper layer of water and another comprising a lower layer of methanesulphonyl fluoride. The phase separation of the distillate can be properly conducted by means of the conventional phase separation manner. For instance, it can be conducted by the conventional phase separation manner by way of optical observation or by means of the conventional phase separation manner by way of electroconductivity measurement. In the case where the upper phase (that is, the water layer) contains methanesulphonyl fluoride, it is recycled to the reaction step of reacting the metal fluoride and methanesulphonyl chloride. By this, the methanesulphonyl fluoride contained in the water layer (that is, the upper phase) can be recovered.

The lower phase (that is, the methanesulphonyl fluoride layer) contains only water as an impurity, and this facilitates the successive purification step. Particularly, the dewatering step is conducted by way of distillation, wherein the initial distillate of about 20 wt. % is removed. And the initial distillate thus removed is recycled to the step of distilling the reaction product obtained as a result of the chemical reaction between the metal fluoride and methanesulphonyl chloride or the phase separation step. By this, high purity methanesulphonyl fluoride is obtained at an improved yield. Thus, the process according to the present invention is markedly advantageous in that the purification step can be effectively conducted by a simple manner by way of distillation.

Incidentally, in the reaction step of conducting chemical reaction between the metal fluoride and methanesulphonyl chloride in the presence of water in a specific amount, there will be an occasion that a slight amount of the methanesulphonyl chloride is remained in the reaction product without being dedicated for the chemical reaction. However, such remainder of methanesulphonyl chloride can be effectively removed in the successive distillation separation step, wherein there are provided a distillate comprising methanesulphonyl chloride, a distillate comprising methanesulphonyl fluoride and a distillate comprising water.

The features and advantages of the present invention will be described in more detail by reference to the following examples and comparative examples. It should be understood that the following examples are provided here for illustrative purposes only and are not intended to restrict the scope of the present invention.

EXAMPLE 1

140 Kg of methanesulphonyl chloride, sodium fluoride (NaF) in an amount of 60 Kg (corresponding to an equivalent weight amount of 1.2 times the amount of the methanesulphonyl chloride), and water in an amount of 420 Kg (corresponding to a part by weight amount of 3 times the amount of the methanesulphonyl chloride) were introduced into the conventional jacket type reaction apparatus of 1 m$^3$ in capacity, wherein they are well mixed, followed by subjecting the mixture to chemical reaction while maintaining the mixture at 50° C. for 4 hours, to obtain a reaction product. The reaction product obtained was subjected to simple distillation at a vacuum of 60 Torr and at 50° C. until no distillate of methanesulphonyl fluoride was observed, to thereby obtain a distillate having two phases one comprising an upper layer of water and another comprising a lower layer of methanesulphonyl fluoride. The resultant distillate was subjected to phase separation by way of optical observation, to thereby separate the lower layer of methanesulphonyl fluoride from the upper layer of water. The separated lower layer of methanesulphonyl fluoride was found to be 113 Kg. And the yield was found to be 94.2%.

The upper layer of water was found to be 75 Kg. And the upper layer of water was found to contain 5.0 Kg of methanesulphonyl fluoride.

The above lower layer of methanesulphonyl fluoride was subjected to simple distillation at a vacuum of 60 Torr and at 50° C., followed by dewatering purification by way of distillation wherein the initial distillate of 20 wt. % was removed. The resultant was found to contain water in a trace amount of 150 ppm. Thus, there was obtained 90 Kg of a dewatered product of methanesulphonyl fluoride.

The conditions employed and the results obtained in this example are collectively shown in Table 1.

EXAMPLE 2

280 Kg of methanesulphonyl chloride, sodium fluoride (NaF) in an amount of 120 Kg (corresponding to an equivalent weight amount of 1.2 times the amount of the methanesulphonyl chloride), and water in an amount of 420 Kg (corresponding to a part by weight amount of 1.5 times the amount of the methanesulphonyl chloride) were introduced into the conventional jacket type reaction apparatus of 1 m$^3$ in capacity, wherein they are well mixed, followed by subjecting the mixture to chemical reaction while maintaining the mixture at 50° C. for 4 hours, to obtain a reaction product. The reaction product obtained was subjected to simple distillation at a vacuum of 60 Torr and at 50° C. until no distillate of methanesulphonyl fluoride was observed, to thereby obtain a distillate having two phases one comprising an upper layer of water and another comprising a lower layer of methanesulphonyl fluoride. The resultant distillate was subjected to phase separation by way of optical observation, to thereby separate the lower layer of methanesulphonyl fluoride from the upper layer of water. The separated lower layer of methanesulphonyl fluoride was found to be 225 Kg. And the yield was found to be 94.0%.

The upper layer of water was found to be 140 Kg. And the upper layer of water was found to contain 9.5 Kg of methanesulphonyl fluoride.

The above lower layer of methanesulphonyl fluoride was subjected to simple distillation at a vacuum of 60 Torr and at 50° C., followed by dewatering purification by way of distillation wherein the initial distillate of 18 wt. % was removed. The resultant was found to contain water in a trace amount of 250 ppm. Thus, there was obtained 180 Kg of a dewatered product of methanesulphonyl fluoride.

The conditions employed and the results obtained in this example are collectively shown in Table 1.

EXAMPLE 3

280 Kg of methanesulphonyl chloride, sodium fluoride (NaF) in an amount of 115 Kg (corresponding to an equivalent amount of 1.2 times the amount of the methanesulphonyl chloride), 300 Kg of water and 140 Kg of the water layer separated in Example 2 (the total water content: 430 Kg which corresponds to a part by weight amount of 1.5 times the amount of the methanesulphonyl chloride) were introduced into the conventional jacket type reaction apparatus of 1 m$^3$ in capacity, wherein they are well mixed, followed by subjecting the mixture to chemical reaction while maintaining the mixture at 50° C. for 4 hours, to obtain a reaction product. The reaction product obtained was subjected to simple distillation at a vacuum of 60 Torr and at 50° C. until no distillate of methanesulphonyl fluoride was observed, to thereby obtain a distillate having two phases one comprising an upper layer of water and another comprising a lower layer of methanesulphonyl fluoride. The resultant distillate was subjected to phase separation by way of optical observation, to thereby separate the lower layer of methanesulphonyl fluoride from the upper layer of water. The separated lower layer of methanesulphonyl fluoride was found to be 233 Kg. And the yield was found to be 97.2%.

The upper layer of water was found to be 145 Kg. And the upper layer of water was found to contain 9.8 Kg of methanesulphonyl fluoride.

The above lower layer of methanesulphonyl fluoride was subjected to simple distillation at a vacuum of 60 Torr and at 50° C., followed by dewatering purification by way of distillation wherein the initial distillate of 18 wt. % was removed. The resultant was found to contain water in a trace amount of 250 ppm. Thus, there was obtained 190 Kg of a dewatered product of methanesulphonyl fluoride.

The conditions employed and the results obtained in this example are collectively shown in Table 1.

EXAMPLE 4

280 Kg of methanesulphonyl chloride, sodium fluoride (NaF) in an amount of 120 Kg (corresponding to an equivalent weight amount of 1.2 times the amount of the methanesulphonyl chloride), and water in an amount of 200 Kg (corresponding to a part by weight amount of 0.7 time weight versus the amount of the methanesulphonyl chloride) were introduced into the conventional jacket type reaction apparatus of 1 m$^3$ in capacity, wherein they are well mixed, followed by subjecting the mixture to chemical reaction while maintaining the mixture at 50° C. for 4 hours, to obtain a reaction product. The reaction product obtained was subjected to simple distillation at a vacuum of 60 Torr and at 50° C. until no distillate of methanesulphonyl fluoride was observed, to thereby obtain a distillate having two phases one comprising an upper layer of water and another comprising a lower layer of methanesulphonyl fluoride. The resultant distillate was subjected to phase separation by way of optical observation, to thereby separate the lower layer of methanesulphonyl fluoride from the upper layer of water. The separated lower layer of methanesulphonyl fluoride was found to be 224 Kg. And the yield was found to be 93.4%.

The upper layer of water was found to be 140 Kg. And the upper layer of water was found to contain 9.5 Kg of methanesulphonyl fluoride.

The above lower layer of methanesulphonyl fluoride was subjected to simple distillation at a vacuum of 60 Torr and at 50° C., followed by dewatering purification by way of distillation wherein the initial distillate of 18 wt. % was removed. The resultant was found to contain water in a trace amount of 250 ppm. Thus, there was obtained 180 Kg of a dewatered product of methanesulphonyl fluoride.

The conditions employed and the results obtained in this example are collectively shown in Table 1.

EXAMPLE 5

280 Kg of methanesulphonyl chloride, sodium fluoride (NaF) in an amount of 115 Kg (corresponding to an equivalent weight amount of 1.1 times the amount of the methanesulphonyl chloride), and water in an amount of 420 Kg (corresponding to a part by weight amount of 1.5 times the amount of the methanesulphonyl chloride) were introduced into the conventional jacket type reaction apparatus of 1 m³ in capacity, wherein they are well mixed, followed by subjecting the mixture to chemical reaction while maintaining the mixture at 50° C. for 4 hours, to obtain a reaction product. The reaction product obtained was subjected to simple distillation at a vacuum of 60 Torr and at 50° C. until no distillate of methanesulphonyl fluoride was observed, to thereby obtain a distillate having two phases one comprising an upper layer of water and another comprising a lower layer of methanesulphonyl fluoride. The resultant distillate was subjected to phase separation by way of optical observation, to thereby separate the lower layer of methanesulphonyl fluoride from the upper layer of water. The separated lower layer of methanesulphonyl fluoride was found to be 227 Kg. The methanesulphonyl fluoride in the lower layer was examined with respect to water content and purity. As a result, it was found that the water content is 1.2 wt. % and the purity is 98.8%. And the yield was found to be 93.5%.

The upper layer of water was found to be 150 Kg. And the upper layer of water was found to contain 10.2 Kg of methanesulphonyl fluoride.

The above lower layer of methanesulphonyl fluoride was subjected to simple distillation at a vacuum of 60 Torr and at 50° C., followed by dewatering purification by way of distillation wherein the initial distillate of 20 wt. % was removed. The resultant was found to contain water in a trace amount of 150 ppm. Thus, there was obtained 182 Kg of a dewatered product of methanesulphonyl fluoride.

The initial distillate removed in the above was found to be 45.4 Kg and contain 42.7 Kg of methanesulphonyl fluoride.

The conditions employed and the results obtained in this example are collectively shown in Table 1.

EXAMPLE 6

280 Kg of methanesulphonyl chloride, sodium fluoride (NaF) in an amount of 115 Kg (corresponding to an equivalent weight amount of 1.1 times the amount of the methanesulphonyl chloride), 300 Kg of water and 150 Kg of the water layer (containing 10.2 Kg of methanesulphonyl fluoride) separated in Example 5, and 45.4 Kg of the initial distillate (containing 42.7 Kg of methanesulphonyl fluoride) removed in Example 5 were introduced into the conventional jacket type reaction apparatus of 1 m³ in capacity, wherein they are well mixed, followed by subjecting the mixture to chemical reaction while maintaining the mixture at 50° C. for 4 hours, to obtain a reaction product. The reaction product obtained was subjected to simple distillation at a vacuum of 60 Torr and at 50° C. until no distillate of methanesulphonyl fluoride was observed, to thereby obtain a distillate having two phases one comprising an upper layer of water and another comprising a lower layer of methanesulphonyl fluoride. The resultant distillate was subjected to phase separation by way of optical observation, to thereby separate the lower layer of methanesulphonyl fluoride from the upper layer of water. The separated lower layer of methanesulphonyl fluoride was found to be 277.6 Kg.

The methanesulphonyl fluoride in the lower layer was examined with respect to water content and purity. As a result, it was found that the water content is 1.0 wt. % and the purity is 99.0%. And the yield (excluding 42.7 Kg of the methanesulphonyl fluoride contained in the above initial distillate) was found to be 96.8%.

The upper layer of water was found to be 150 Kg. And the upper layer of water was found to contain 10.3 Kg of methanesulphonyl fluoride.

The conditions employed and the results obtained in this example are collectively shown in Table 1.

Comparative Example 1

280 Kg of methanesulphonyl chloride, sodium fluoride (NaF) in an amount of 120 Kg (corresponding to an equivalent weight amount of 1.2 times the amount of the methanesulphonyl chloride), and water in an amount of 185 Kg (corresponding to a part by weight amount of 0.65 time the amount of the methanesulphonyl chloride) were introduced into the conventional jacket type reaction apparatus of 1 m³ in capacity, wherein they are well mixed, followed by subjecting the mixture to chemical reaction while maintaining the mixture at 50° C. for 4 hours, to obtain a reaction product. The reaction product obtained was subjected to simple distillation at a vacuum of 60 Torr and at 50° C. until no distillate of methanesulphonyl fluoride was observed, to thereby obtain a distillate having two phases one comprising an upper layer of water and another comprising a lower layer of methanesulphonyl fluoride. The resultant distillate was subjected to phase separation by way of optical observation, to thereby separate the lower layer of methanesulphonyl fluoride from the upper layer of water. The separated lower layer of methanesulphonyl fluoride was found to be 192 Kg. And the yield was found to be 80.0%.

The upper layer of water was found to be 130 Kg. And the upper layer of water was found to contain 8.8 Kg of methanesulphonyl fluoride.

The above lower layer of methanesulphonyl fluoride was subjected to simple distillation at a vacuum of 60 Torr and at 50° C., followed by dewatering purification by way of distillation wherein the initial distillate of 18 wt. % was removed. The resultant was found to contain water in a trace amount of 250 ppm. Thus, there was obtained 155 Kg of a dewatered product of methanesulphonyl fluoride.

The conditions employed and the results obtained in this comparative example are collectively shown in Table 1.

Comparative Example 2

280 Kg of methanesulphonyl chloride, sodium fluoride (NaF) in an amount of 115 Kg (corresponding to an equivalent weight amount of 1.1 times the amount of the methanesulphonyl chloride), and water in an amount of 170 Kg (corresponding to a part by weight amount of 0.6 time the amount of the methanesulphonyl chloride) were introduced into the conventional jacket type reaction apparatus of 1 m$^3$ in capacity, wherein they are well mixed, followed by subjecting the mixture to chemical reaction while maintaining the mixture at 50° C. for 4 hours, to obtain a reaction product. The reaction product obtained was subjected to simple distillation at a vacuum of 60 Torr and at 50° C. until no distillate of methanesulphonyl fluoride was observed, to thereby obtain a distillate having two phases one comprising an upper layer of water and another comprising a lower layer of methanesulphonyl fluoride. The resultant distillate was subjected to phase separation by way of optical observation, to thereby separate the lower layer of methanesulphonyl fluoride from the upper layer of water. The separated lower layer of methanesulphonyl fluoride was found to be 198 Kg. And the yield was found to be 79.0%.

The upper layer of water was found to be 130 Kg. And the upper layer of water was found to contain 8.7 Kg of methanesulphonyl fluoride.

The above lower layer of methanesulphonyl fluoride was subjected to simple distillation at a vacuum of 60 Torr and at 50° C., followed by dewatering purification by way of distillation wherein the initial distillate of 18 wt. % was removed. The resultant was found to contain water in a trace amount of 250 ppm. Thus, there was obtained 154 Kg of a dewatered product of methanesulphonyl fluoride.

The conditions employed and the results obtained in this comparative example are collectively shown in Table 1.

EXAMPLE 7

140 Kg of methanesulphonyl chloride, potassium fluoride (KF) in an amount of 76 Kg (corresponding to an equivalent weight amount of 1.1 times the amount of the methanesulphonyl chloride), and water in an amount of 420 Kg (corresponding to a part by weight amount of 3.0 times weight versus the amount of the methanesulphonyl chloride) were introduced into the conventional jacket type reaction apparatus of 1 m$^3$ in capacity, wherein they are well mixed, followed by subjecting the mixture to chemical reaction while maintaining the mixture at 50° C. for 4 hours, to obtain a reaction product. The reaction product obtained was subjected to simple distillation at a vacuum of 60 Torr and at 50° C. until no distillate of methanesulphonyl fluoride was observed, to thereby obtain a distillate having two phases one comprising an upper layer of water and another comprising a lower layer of methanesulphonyl fluoride. The resultant distillate was subjected to phase separation by way of optical observation, to thereby separate the lower layer of methanesulphonyl fluoride from the upper layer of water. The separated lower layer of methanesulphonyl fluoride was found to be 113 Kg. And the yield was found to be 94.0%.

The upper layer of water was found to be 75 Kg. And the upper layer of water was found to contain 5.1 Kg of methanesulphonyl fluoride.

The above lower layer of methanesulphonyl fluoride was subjected to simple distillation at a vacuum of 60 Torr and at 50° C., followed by dewatering purification by way of distillation wherein the initial distillate of 18 wt. % was removed. The resultant was found to contain water in a trace amount of 250 ppm. Thus, there was obtained 90 Kg of a dewatered product of methanesulphonyl fluoride.

The conditions employed and the results obtained in this example are collectively shown in Table 1.

EXAMPLE 8

280 Kg of methanesulphonyl chloride, potassium fluoride (KF) in an amount of 156 Kg (corresponding to an equivalent weight amount of 1.1 times the amount of the methanesulphonyl chloride), and water in an amount of 420 Kg (corresponding to a part by weight amount of 1.5 times the amount of the methanesulphonyl chloride) were introduced into the conventional jacket type reaction apparatus of 1 m$^3$ in capacity, wherein they are well mixed, followed by subjecting the mixture to chemical reaction while maintaining the mixture at 50° C. for 4 hours, to obtain a reaction product. The reaction product obtained was subjected to simple distillation at a vacuum of 60 Torr and at 50° C. until no distillate of methanesulphonyl fluoride was observed, to thereby obtain a distillate having two phases one comprising an upper layer of water and another comprising a lower layer of methanesulphonyl fluoride. The resultant distillate was subjected to phase separation by way of optical observation, to thereby separate the lower layer of methanesulphonyl fluoride from the upper layer of water. The separated lower layer of methanesulphonyl fluoride was found to be 227 Kg. And the yield was found to be 94.8%.

The upper layer of water was found to be 140 Kg. And the upper layer of water was found to contain 9.5 Kg of methanesulphonyl fluoride.

The above lower layer of methanesulphonyl fluoride was subjected to simple distillation at a vacuum of 60 Torr and at 50° C., followed by dewatering purification by way of distillation wherein the initial distillate of 18 wt. % was removed. The resultant was found to contain water in a trace amount of 250 ppm. Thus, there was obtained 186 Kg of a dewatered product of methanesulphonyl fluoride.

The conditions employed and the results obtained in this example are collectively shown in Table 1.

EXAMPLE 9

280 Kg of methanesulphonyl chloride, potassium fluoride (KF) in an amount of 156 Kg (corresponding to an equivalent weight amount of 1.1 times the amount of the methanesulphonyl chloride), and 150 Kg of water were introduced into the conventional jacket type reaction apparatus of 1 m$^3$ in capacity, wherein they are well mixed, followed by subjecting the mixture to chemical reaction while maintaining the mixture at 50° C. for 4 hours, to obtain a reaction product. 50 Kg of water was then added to the reaction product (the total water content: 200 Kg which corresponds to a part by weight amount of 0.7 time weight versus the amount of the KF). The resultant was subjected to simple distillation at a vacuum of 60 Torr and at 50° C. until no distillate of methanesulphonyl fluoride was observed, to thereby obtain a distillate having two phases one comprising an upper layer of water and another comprising a lower layer of methanesulphonyl fluoride. The resultant distillate was subjected to phase separation by way of optical observation, to thereby separate the lower layer of methanesulphonyl fluoride from the upper layer of water. The separated lower layer of methanesulphonyl fluoride was found to be 228 Kg. And the yield was found to be 95.2%.

The upper layer of water was found to be 140 Kg. And the upper layer of water was found to contain 9.5 Kg of methanesulphonyl fluoride.

The above lower layer of methanesulphonyl fluoride was subjected to simple distillation at a vacuum of 60 Torr and at 50° C., followed by dewatering purification by way of distillation wherein the initial distillate of 18 wt. % was removed. The resultant was found to contain water in a trace amount of 250 ppm. Thus, there was obtained 187 Kg of a dewatered product of methanesulphonyl fluoride.

The conditions employed and the results obtained in this example are collectively shown in Table 1.

Comparative Example 3

280 Kg of methanesulphonyl chloride, potassium fluoride (KF) in an amount of 156 Kg (corresponding to an equivalent weight amount of 1.1 times the amount of the methanesulphonyl chloride), and water in an amount of 185 Kg (corresponding to a part by weight amount of 0.65 time the amount of the methanesulphonyl chloride) were introduced into the conventional jacket type reaction apparatus of 1 m$^3$ in capacity, wherein they are well mixed, followed by subjecting the mixture to chemical reaction while maintaining the mixture at 50° C. for 4 hours, to obtain a reaction product. The reaction product obtained was subjected to simple distillation at a vacuum of 60 Torr and at 50° C. until no distillate of methanesulphonyl fluoride was observed, to thereby obtain a distillate having two phases one comprising an upper layer of water and another comprising a lower layer of methanesulphonyl fluoride. The resultant distillate was subjected to phase separation by way of optical observation, to thereby separate the lower layer of methanesulphonyl fluoride from the upper layer of water. The separated lower layer of methanesulphonyl fluoride was found to be 201 Kg. And the yield was found to be 84.0%.

The upper layer of water was found to be 135 Kg. And the upper layer of water was found to contain 9.1 Kg of methanesulphonyl fluoride.

The above lower layer of methanesulphonyl fluoride was subjected to simple distillation at a vacuum of 60 Torr and at 50° C., followed by dewatering purification by way of distillation wherein the initial distillate of 18 wt. % was removed. The resultant was found to contain water in a trace amount of 250 ppm. Thus, there was obtained 164 Kg of a dewatered product of methanesulphonyl fluoride.

The conditions employed and the results obtained in this comparative example are collectively shown in Table 1.

Comparative Example 4

280 Kg of methanesulphonyl chloride, potassium fluoride (KF) in an amount of 156 Kg (corresponding to an equivalent weight amount of 1.1 times the amount of the methanesulphonyl chloride), and water in an amount of 170 Kg (corresponding to a part by weight amount of 0.6 time weight versus the amount of the methanesulphonyl chloride) were introduced into the conventional jacket type reaction apparatus of 1 m$^3$ in capacity, wherein they are well mixed, followed by subjecting the mixture to chemical reaction while maintaining the mixture at 50° C. for 4 hours, to obtain a reaction product. The reaction product obtained was subjected to simple distillation at a vacuum of 60 Torr and at 50° C. until no distillate of methanesulphonyl fluoride was observed, to thereby obtain a distillate having two phases one comprising an upper layer of water and another comprising a lower layer of methanesulphonyl fluoride. The resultant distillate was subjected to phase separation by way of optical observation, to thereby separate the lower layer of methanesulphonyl fluoride from the upper layer of water. The separated lower layer of methanesulphonyl fluoride was found to be 199 Kg. And the yield was found to be 83.0%.

The upper layer of water was found to be 135 Kg. And the upper layer of water was found to contain 9.2 Kg of methanesulphonyl fluoride.

The above lower layer of methanesulphonyl fluoride was subjected to simple distillation at a vacuum of 60 Torr and at 50° C., followed by dewatering purification by way of distillation wherein the initial distillate of 20 wt. % was removed. The resultant was found to contain water in a trace amount of 180 ppm. Thus, there was obtained 159 Kg of a dewatered product of methanesulphonyl fluoride.

The conditions employed and the results obtained in this comparative example are collectively shown in Table 1.

TABLE 1

| | Production of $CH_3SO_2F$ | | | | | | | | |
|---|---|---|---|---|---|---|---|---|---|
| | $CH_3SO_2Cl$ | | fluorinating agent | | molar ratio | $H_2O$ | weight ratio | yield | |
| No. | (kg) | (kmol) | | (kg) | (kmol) | (*-1) | (kg) | (*-2) | (%) | evaluation |
| Example 1 | 140 | 1.2 | NaF | 60 | 1.4 | 1.2 | 420 | 3.0 | 94.2 | ○ |
| Example 2 | 280 | 2.4 | NaF | 120 | 2.9 | 1.2 | 420 | 1.5 | 94.0 | ○ |
| Example 3 | 280 | 2.4 | NaF | 115 | 2.7 | 1.1 | 430 | 1.5 | 97.2 | ◉ |
| Example 4 | 280 | 2.4 | NaF | 120 | 2.9 | 1.2 | 200 | 0.7 | 93.4 | ○ |
| Example 5 | 280 | 2.4 | NaF | 115 | 2.7 | 1.1 | 420 | 1.5 | 93.5 | ○ |
| Example 6 | 280 | 2.4 | NaF | 115 | 2.7 | 1.1 | 440 | 1.6 | 96.8 | ◉ |
| Comparative Example 1 | 280 | 2.4 | NaF | 120 | 2.9 | 1.2 | 185 | 0.65 | 80.0 | △ |
| Comparative Example 2 | 280 | 2.4 | NaF | 115 | 2.7 | 1.1 | 170 | 0.6 | 79.0 | △ |
| Example 7 | 140 | 1.2 | KF | 76 | 1.3 | 1.1 | 420 | 3.0 | 94.0 | ○ |
| Example 8 | 280 | 2.4 | KF | 156 | 2.6 | 1.1 | 420 | 1.5 | 94.8 | ○ |
| Example 9 | 280 | 2.4 | KF | 156 | 2.6 | 1.1 | 200 | 0.7 | 95.2 | ◉ |
| Comparative Example 3 | 280 | 2.4 | KF | 156 | 2.6 | 1.1 | 185 | 0.65 | 84.0 | △ |
| Comparative Example 4 | 280 | 2.4 | KF | 156 | 2.6 | 1.1 | 170 | 0.6 | 83.0 | △ |

*-1: versus $CH_3SO_2Cl$
*-2: versus $CH_3SO_2Cl$
△: ordinary yield in the prior art
○: supeior yield
◉: markedly superior yield As apparent from the results shown in Table 1, it is understood that any of Examples 1 to 9 according to the present invention in which the reaction product between methanesulphonyl chloride as the starting material and a given metal fluoride (NaF or KF) was distilled to recover a final product (methanesulphonyl fluoride) in the presence water in a relatively greater amount (specifically, in a part by weight amount of 0.7 time or above the amount of the methanesulphonyl chloride used) is surpassing any of Comparative Examples 1 to 4 in which the reaction product between methanesulphonyl chloride as the starting material and a given metal fluoride (NaF or KF) was distilled in the presence water in a relatively smaller amount (specifically, in an amount of less than 0.7 time versus the amount of the methanesulphonyl chloride used), in terms of the yield of methanesulphonyl fluoride as the final product. As for the reason why the yield of the final product (that is, methanesulphonyl fluoride) is inferior in any of the comparative examples, it is considered that a certain amount of the methanesulphonyl chloride as the starting material is remained because the water content of the reaction product upon the distillation is not sufficient.

What is claimed is:

1. A process for producing methanesulphonyl fluoride, comprising the steps of:
   (a) reacting methanesulphonyl chloride, a fluoride compound and water to obtain a reaction product containing methanesulphonyl fluoride and impurities including water and by-products, the amount of said water as a starting material such that said reaction product contains water in an amount corresponding to 0.7 part by weight or above versus the amount of said methanesulphonyl chloride as a starting material upon subjecting said reaction product to distillation;
   (b) subjecting said reaction product to distillation to obtain a distillate free of said by-products, said distillate comprising (b-i) a water layer, and (b-ii) a methanesulphonyl fluoride layer which contains a minor amount of water as an impurity;
   (c) subjecting said distillate obtained in step (b) to phase separation to separate said layer (b-ii) from said layer (b-i); and
   (d) subjecting the separated layer (b-ii) to distillation and removing an initial part of a distillate obtained, to thereby obtain a product of methanesulfonyl fluoride that is substantially free of water.

2. The process according to claim 1, wherein the initial part removed in step (d) is in an amount of 18 wt. % or more of the total amount of the distillate obtained in step (d).

3. The process according to claim 1, wherein the fluoride compound is a compound selected from the group consisting of alkali metal fluorides, acidic alkali metal fluorides, $NH_4F$, $(NH_4)_2SiF_6$, $H_2SiF_6$, $Na_2SiF_6$, and HF.

4. The process according to claim 1, further comprising recycling water from the water layer (b-i) separated in step (c) to be used in step (a).

5. The process according to claim 1, further comprising recycling the initial part removed in step (d) to step (c), wherein the initial part is added to the distillate subjected to phase separation.

* * * * *